(12) United States Patent
Nakamura et al.

(10) Patent No.: US 9,000,005 B2
(45) Date of Patent: Apr. 7, 2015

(54) HIGHLY PURE PYRROLOQUINOLINYL-PYRROLE-2,5-DIONE AND PYRROLOQUINOLINYL-PYRROLIDINE-2,5-DIONE AND METHODS OF PREPARING SAME

(71) Applicant: ArQule, Inc., Woburn, MA (US)

(72) Inventors: Yoshitaka Nakamura, Kanagawa (JP); Jo Ooyama, Kanagawa (JP)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 13/788,271

(22) Filed: Mar. 7, 2013

(65) Prior Publication Data

US 2013/0281699 A1    Oct. 24, 2013

Related U.S. Application Data

(60) Provisional application No. 61/637,139, filed on Apr. 23, 2012.

(51) Int. Cl.
| | | |
|---|---|---|
| C07D 471/06 | (2006.01) | |
| C07D 451/00 | (2006.01) | |
| C07D 453/00 | (2006.01) | |
| C07D 455/00 | (2006.01) | |
| A61K 31/473 | (2006.01) | |

(52) U.S. Cl.
CPC .................................... *C07D 471/06* (2013.01)

(58) Field of Classification Search
USPC .......................................... 514/294; 546/192
See application file for complete search history.

(56) References Cited

U.S. PATENT DOCUMENTS

| | | | |
|---|---|---|---|
| 6,867,198 B2 * | 3/2005 | Al-Awar et al. ............ 514/44 R |
| 7,713,969 B2 | 5/2010 | Li et al. | |
| 8,377,927 B2 | 2/2013 | Li et al. | |
| 2010/0297075 A1 | 11/2010 | Chan et al. | |
| 2011/0160242 A1 | 6/2011 | Reed et al. | |
| 2013/0011481 A1 | 1/2013 | Yamakose et al. | |

OTHER PUBLICATIONS

Loewenthal; "A Guide for the Perplexed Organic Experimentalist" Second Edition, 1990, Wiley & Sons.*
Beviglia et al. "Expression of the c-Met/HGF Receptor in Human Breast Carcinoma: Correlation with Tumor Progression." *Int. J. Cancer.* 74.3(1997):301-309.
Danilkovitch-Miagkova et al. "Dysregulation of Met Receptor Tyrosine Kinase Activity in Invasive Tumors." *J. Clin. Invest.* 109(2002):863-867.
Faul et al. "A New, Efficient Method of the Synthesis of Bisindolylmaleim ides." *J. Org. Chem.* 63.17(1998):6053-6058.
Ma et al. "c-Met: Structure, Functions and Potential for Therapeutic Inhibition." *Cancer Metastasis Rev.* 22.4(2003):309-325.
Qian et al., "Met Protein Expression Level Correlates with Survival in Patients with Late-stage Nasopharyngeal Carcinoma", *Cancer Res.*, 62:589-596 (2002).
Qiao et al. "Constitutive Activation of Met Kinase in Non-Small-Cell Lung Carcinomas Correlates with Anchorage-Independent Cell Survival." *J. Cell. Biochem.* 86.4(2002):665-677.
Takeuchi et al. "c-Met Expression Level in Primary Colon Cancer: A Predictor of Tumor Invasion and Lymph Node Metastases." *Clin. Cancer Res.* 9.4(2003):1480-1488.
Zhang et al. "Met Decoys: Will Cancer Take the Bait?" *Cancer Cell.* 6.1(2004):5-6.

* cited by examiner

*Primary Examiner* — John Mabry
*Assistant Examiner* — Daniel Carcanague
(74) *Attorney, Agent, or Firm* — Cooley LLP; Ivor R. Elrifi; Matthew Pavao

(57) ABSTRACT

The present invention relates to highly-pure pyrroloquinolinyl-pyrrole-2,5-dione and pyrroloquinolinyl-pyrrolidine-2,5-dione, for example, 3-(5,6-dihydro-4H-pyrrolo[3,2,1-ij]quinolin-1-yl)-4-(1H-indol-3-yl)-1H-pyrrole-2,5-dione, 3-(5,6-dihydro-4H-pyrrolo[3,2,1-ij]quinolin-1-yl)-4-(1H-indol-3-yl)pyrrolidine-2,5-dione, and pharmaceutically acceptable salts, solvates, and diastereomers thereof. The present invention also relates to methods for preparing highly-pure pyrroloquinolinyl-pyrrole-2,5-dione and pyrroloquinolinyl-pyrrolidine-2,5-dione, for example, 3-(5,6-dihydro-4H-pyrrolo[3,2,1-ij]quinolin-1-yl)-4-(1H-indol-3-yl)-1H-pyrrole-2,5-dione, 3-(5,6-dihydro-4H-pyrrolo[3,2,1-ij]quinolin-1-yl)-4-(1H-indol-3-yl)pyrrolidine-2,5-dione, and pharmaceutically acceptable salts, solvates, and diastereomers thereof.

24 Claims, No Drawings

US 9,000,005 B2

HIGHLY PURE PYRROLOQUINOLINYL-PYRROLE-2,5-DIONE AND PYRROLOQUINOLINYL-PYRROLIDINE-2,5-DIONE AND METHODS OF PREPARING SAME

CROSS-REFERENCE TO RELATED APPLICATION

This application claims priority to, and the benefit of, U.S. Ser. No. 61/637,139, filed on Apr. 23, 2012, the contents of which are incorporated herein by reference in their entirety.

BACKGROUND OF THE INVENTION

Cancer is the second leading cause of death in the United States, exceeded only by heart disease (*Cancer Facts and Figures* 2004, American Cancer Society, Inc.). Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational mechanisms may lead to the development of cancer. As such, heterogeneity frequently exists between cancer cells taken from tumors of the same tissue and same histotype that have originated in different individuals. Frequently observed mutational mechanisms associated with some cancers may differ between one tissue type and another (e.g., frequently observed mutational mechanisms leading to colon cancer may differ from frequently observed mechanisms leading to leukemias). It is therefore often difficult to predict whether a particular cancer will respond to a particular chemo-therapeutic agent (*Cancer Medicine*, 5th Edition, Bast et al. eds., B. C. Decker Inc., Hamilton, Ontario).

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extracellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are dysregulated in human cancers, and may contribute to dysregulation of cell growth, tumor cell dissemination, and tumor invasion during disease progression and metastasis (see, e.g., *Journal of Clinical Investigation* 109: 863-867 (2002) and *Cancer Cell* pp 5-6 Jul. 2004). c-Met and HGF are highly expressed relative to surrounding tissue in numerous cancers, and their expression correlates with poor patient prognosis (see, e.g., *Journal of Cellular Biochemistry* 86: 665-677 (2002); *Int. J. Cancer* (*Pred. Oncol.*) 74: 301-309 (1997); *Clinical Cancer Research* 9: 1480-1488 (2003); and *Cancer Research* 62: 589-596 (2002)). Without intending to be bound by theory, c-Met and HGF may protect tumors against cell death induced by DNA damaging agents, and as such may contribute to chemoresistance and radioresistance of tumors. Without intending to be limited by any theory, inhibitors of c-Met may be useful as therapeutic agents in the treatment of proliferative disorders including breast cancer (see, e.g., *Cancer and Metastasis Reviews* 22: 309-325 (2003)). Accordingly, new compounds and methods for modulating these factors and treating cancer are needed. The present invention addresses these needs.

SUMMARY OF THE INVENTION

The present invention relates to highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof.

In one embodiment, the pyrroloquinolinyl-pyrrole-2,5-dione and pyrroloquinolinyl-pyrrolidine-2,5-dione each independently have a purity of at least 70%, 75%, 80%, 85%, 88%, 90%, 91%, 92%, 93%, 94%, 95%, 96%, 97%, 98%, 99%, 99.5%, 99.8%, 99.9%.

In one embodiment, the pyrroloquinolinyl-pyrrole-2,5-dione and pyrroloquinolinyl-pyrrolidine-2,5-dione each independently contain less than 30%, 25%, 20%, 15%, 12%, 10%, 9%, 8%, 7%, 6%, 5%, 4%, 3%, 2%, 1%, 0.5%, 0.2%, or 0.1% impurities. In one embodiment, the impurities comprise 5,6-dihydro-4H-pyrrolo[3,2,1-ij]quinolin-1-yl-oxoacetamide, or a polymer by-product, or a combination thereof.

In one embodiment, the pyrroloquinolinyl-pyrrole-2,5-dione of the present invention is 3-(5,6-dihydro-4H-pyrrolo[3,2,1-ij]quinolin-1-yl)-4-(1H-indol-3-yl)-1H-pyrrole-2,5-dione, or pharmaceutically acceptable salts, solvates, diastereomers, and polymorphs thereof.

In one embodiment, the pyrroloquinolinyl-pyrrolidine-2,5-dione of the present invention is 3-(5,6-dihydro-4H-pyrrolo[3,2,1-ij]quinolin-1-yl)-4-(1H-indol-3-yl)pyrrolidine-2,5-dione, or pharmaceutically acceptable salts, solvates, diastereomers, and polymorphs thereof. In one embodiment, the pyrroloquinolinyl-pyrrolidine-2,5-dione of the present invention is (3S,4R)-3-(5,6-dihydro-4H-pyrrolo[3,2,1-ij]quinolin-1-yl)-4-(1H-indol-3-yl)pyrrolidine-2,5-dione, (3R,4R)-3-(5,6-dihydro-4H-pyrrolo[3,2,1-ij]quinolin-1-yl)-4-(1H-indol-3-yl)pyrrolidine-2,5-dione, (3S,4S)-3-(5,6-dihydro-4H-pyrrolo[3,2,1-ij]quinolin-1-yl)-4-(1H-indol-3-yl)pyrrolidine-2,5-dione, or (3R,4S)-3-(5,6-dihydro-4H-pyrrolo[3,2,1-ij]quinolin-1-yl)-4-(1H-indol-3-yl)pyrrolidine-2,5-dione, or pharmaceutically acceptable salts, solvates or polymorphs thereof. In a further embodiment, the pyrroloquinolinyl-pyrrole-2,5-dione of the present invention is (3R,4R)-3-(5,6-dihydro-4H-pyrrolo[3,2,1-ij]quinolin-1-yl)-4-(1H-indol-3-yl)pyrrolidine-2,5-dione, or pharmaceutically acceptable salts, solvates, or polymorphs thereof.

The present invention also relates to methods for preparing highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof.

In one embodiment, the method of the present invention comprises a step of dissolving methyl pyrroloquinolinyl-oxoacetate and acetamide in an organic solvent and adding the obtained solution to a base, and reacting methylpyrroloquinolinyl-oxoacetate and acetamide to form highly pure pyrroloquinolinyl-pyrrole-2,5-dione. In one embodiment, the base is dissolved or suspended in an organic solvent. In a further embodiment, the base is dissolved or suspended in the same organic solvent as methylpyrroloquinolinyl-oxoacetate and acetamide. In a further embodiment, highly pure pyrroloquinolinyl-pyrrolidine-2,5-dione is formed by reducing pyrroloquinolinyl-pyrrole-2,5-dione.

In one embodiment, the method of the present invention comprises a step of dissolving methyl 5,6-dihydro-4H-pyrrolo[3,2,1-ij]quinolin-1-yl-oxoacetate and indole-3-acetamide in an organic solvent and adding the obtained solution to a base, and reacting methyl 5,6-dihydro-4H-pyrrolo[3,2,1-ij]quinolin-1-yl-oxoacetate and indole-3-acetamide to form highly pure 3-(5,6-dihydro-4H-pyrrolo[3,2,1-ij]quinolin-1-yl)-4-(1H-indol-3-yl)-1H-pyrrole-2,5-dione. In one embodiment, the base is dissolved or suspended in an organic solvent. In a further embodiment, the base is dissolved or suspended in the same organic solvent as methyl 5,6-dihydro-4H-pyrrolo[3,2,1-ij]quinolin-1-yl-oxoacetate and indole-3-acetamide. In a further embodiment, highly pure 3-(5,6-dihydro-4H-pyrrolo[3,2,1-ij]quinolin-1-yl)-4-(1H-indol-3-yl)-1H-pyrrolidine-2,5-dione is formed by reducing 3-(5,6-dihydro-4H-pyrrolo[3,2,1-ij]quinolin-1-yl)-4-(1H-indol-3-yl)-1H-pyrrole-2,5-dione.

The present invention also relates to a pharmaceutical composition comprising the highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof, and a pharmaceutically acceptable carrier.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

DETAILED DESCRIPTION OF THE INVENTION

1. Compounds of the Present Invention

The present invention relates to highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof.

In one embodiment, the pyrroloquinolinyl-pyrrole-2,5-dione and pyrroloquinolinyl-pyrrolidine-2,5-dione each independently have a purity of at least 70%, 75%, 80%, 85%, 88%, 90%, 91%, 92%, 93%, 94%, 95%, 96%, 97%, 98%, 99%, 99.5%, 99.8%, 99.9%. In a further embodiment, the pyrroloquinolinyl-pyrrole-2,5-dione and pyrroloquinolinyl-pyrrolidine-2,5-dione each independently have a purity of at least 95% or 99.5%.

In one embodiment, the pyrroloquinolinyl-pyrrole-2,5-dione and pyrroloquinolinyl-pyrrolidine-2,5-dione each independently contain less than 30%, 25%, 20%, 15%, 12%, 10%, 9%, 8%, 7%, 6%, 5%, 4%, 3%, 2%, 1%, 0.5%, 0.2%, or 0.1% impurities. In one embodiment, the impurities comprise 5,6-dihydro-4H-pyrrolo[3,2,1-ij]quinolin-1-yl-oxoacetamide, or oligomeric by-products, or a combination thereof.

In one embodiment, the pyrroloquinolinyl-pyrrole-2,5-dione and pyrroloquinolinyl-pyrrolidine-2,5-dione each independently contain less than 30%, 25%, 20%, 15%, 12%, 10%, 9%, 8%, 7%, 6%, 5%, 4%, 3%, 2%, 1%, 0.5%, 0.2%, or 0.1% of 5,6-dihydro-4H-pyrrolo[3,2,1-ij]quinolin-1-yl-oxoacetamide. In a further embodiment, the pyrroloquinolinyl-pyrrole-2,5-dione and pyrroloquinolinyl-pyrrolidine-2,5-dione each independently contain less than 2%, 1%, 0.5%, 0.2%, or 0.1% of 5,6-dihydro-4H-pyrrolo[3,2,1-ij]quinolin-1-yl-oxoacetamide.

In one embodiment, the pyrroloquinolinyl-pyrrole-2,5-dione and pyrroloquinolinyl-pyrrolidine-2,5-dione each independently contain less than 30%, 25%, 20%, 15%, 12%, 10%, 9%, 8%, 7%, 6%, 5%, 4%, 3%, 2%, 1%, 0.5%, 0.2%, or 0.1% of oligomeric by-products. In a further embodiment, the pyrroloquinolinyl-pyrrole-2,5-dione and pyrroloquinolinyl-pyrrolidine-2,5-dione each independently contain less than 6%, 5%, 4%, 3%, 2%, 1%, 0.5%, 0.2%, or 0.1% of oligomeric by-products.

In one embodiment, the pyrroloquinolinyl-pyrrole-2,5-dione of the present invention is 3-(5,6-dihydro-4H-pyrrolo[3,2,1-ij]quinolin-1-yl)-4-(1H-indol-3-yl)-1H-pyrrole-2,5-dione having the following structure:

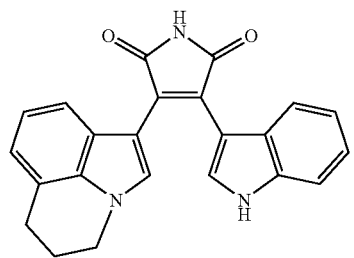 [SMILES: O=C1NC(=O)C(c2cn3c4c(cccc24)CCC3)=C1c1c[nH]c2ccccc12]

or pharmaceutically acceptable salts, solvates, diastereomers, or polymorphs thereof.

In one embodiment, the pyrroloquinolinyl-pyrrolidine-2,5-dione of the present invention is 3-(5,6-dihydro-4H-pyrrolo[3,2,1-ij]quinolin-1-yl)-4-(1H-indol-3-yl)pyrrolidine-2,5-dione having the following structure:

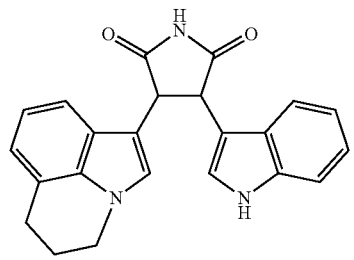 [SMILES: O=C1NC(=O)C(c2cn3c4c(cccc24)CCC3)C1c1c[nH]c2ccccc12]

or pharmaceutically acceptable salts, solvates, diastereomers, or polymorphs thereof.

In one embodiment, the pyrroloquinolinyl-pyrrolidine-2,5-dione of the present invention is:

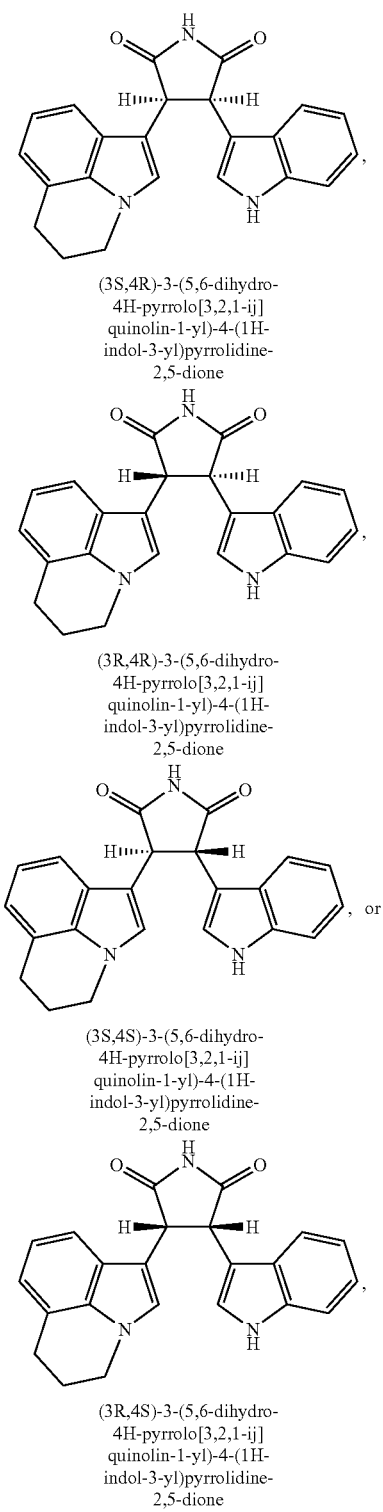

(3S,4R)-3-(5,6-dihydro-
4H-pyrrolo[3,2,1-ij]
quinolin-1-yl)-4-(1H-
indol-3-yl)pyrrolidine-
2,5-dione (3R,4R)-3-(5,6-dihydro-
4H-pyrrolo[3,2,1-ij]
quinolin-1-yl)-4-(1H-
indol-3-yl)pyrrolidine-
2,5-dione (3S,4S)-3-(5,6-dihydro-
4H-pyrrolo[3,2,1-ij]
quinolin-1-yl)-4-(1H-
indol-3-yl)pyrrolidine-
2,5-dione (3R,4S)-3-(5,6-dihydro-
4H-pyrrolo[3,2,1-ij]
quinolin-1-yl)-4-(1H-
indol-3-yl)pyrrolidine-
2,5-dione or pharmaceutically acceptable salts, solvates, or polymorphs thereof. In a further embodiment, the pyrroloquinolinyl-pyrrolidine-2,5-dione of the present invention is (3R,4R)-3-(5,6-dihydro-4H-pyrrolo[3,2,1-ij]quinolin-1-yl)-4-(1H-indol-3-yl)pyrrolidine-2,5-dione, or pharmaceutically acceptable salts, solvates, or polymorphs thereof.

In one embodiment, the salts of pyrroloquinolinyl-pyrrole-2,5-dione and pyrroloquinolinyl-pyrrolidine-2,5-dione of the present application include inorganic salts. For example, the inorganic salt is a potassium or sodium salt. In another embodiment, the salts of pyrroloquinolinyl-pyrrole-2,5-dione and pyrroloquinolinyl-pyrrolidine-2,5-dione of the present application include organic salts. For example, the organic salt is an amine salt, an ephedrine salt, a pseudoephedrine salt, a norephedrine salt, or a 2-methylaminocyclohexanol salt.

In one embodiment, the solvates of pyrroloquinolinyl-pyrrole-2,5-dione and pyrroloquinolinyl-pyrrolidine-2,5-dione of the present application include hydrate, ethanol solvate, heptane solvate, methylene chloride solvate. In one embodiment, the pyrroloquinolinyl-pyrrole-2,5-dione and pyrroloquinolinyl-pyrrolidine-2,5-dione of the present application are each independently present as a hydrate.

2. Methods of the Present Invention

The present invention also relates to methods for preparing highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof.

In one embodiment, the method of the present invention comprises a step of dissolving methyl pyrroloquinolinyl-oxoacetate and acetamide in an organic solvent and adding the obtained solution to a base, and reacting methylpyrroloquinolinyl-oxoacetate and acetamide to form highly pure pyrroloquinolinyl-pyrrole-2,5-dione. In one embodiment, the base is dissolved or suspended in an organic solvent. In a further embodiment, the base is dissolved or suspended in the same organic solvent as methylpyrroloquinolinyl-oxoacetate and acetamide. In a further embodiment, highly pure pyrroloquinolinyl-pyrrolidine-2,5-dione is formed by reducing pyrroloquinolinyl-pyrrole-2,5-dione.

In one embodiment, the method of the present invention comprises a step of dissolving methyl 5,6-dihydro-4H-pyrrolo[3,2,1-ij]quinolin-1-yl-oxoacetate and indole-3-acetamide in an organic solvent and adding the obtained solution to a base, and reacting methyl 5,6-dihydro-4H-pyrrolo[3,2,1-ij]quinolin-1-yl-oxoacetate and indole-3-acetamide to form highly pure 3-(5,6-dihydro-4H-pyrrolo[3,2,1-ij]quinolin-1-yl)-4-(1H-indol-3-yl)-1H-pyrrole-2,5-dione.

The solvent can be any solvent which dissolves 5,6-dihydro-4H-pyrrolo[3,2,1-ij]quinolin-1-yl-oxoacetate and indole-3-acetamide to some extent. In one embodiment, the solvent does not impair the reaction between 5,6-dihydro-4H-pyrrolo[3,2,1-ij]quinolin-1-yl-oxoacetate and indole-3-acetamide. For example, the solvent is an ether, including but not limited to, dimethyl ether, diethyl ether, and tetrahydrofuran (THF), or a hydrocarbon, including but not limited to, toluene and hexane, or an amide, including but not limited to, dimethylformamide (DMF) and dimethylacetamide. In a preferred embodiment, the solvent is an ether. In a more preferred embodiment, the solvent is THF.

The ratio of the amount of indole-3-acetamide and the amount of 5,6-dihydro-4H-pyrrolo[3,2,1-ij]quinolin-1-yl-oxoacetate can be 0.5-2.0, 0.6-1.6, 0.7-1.4, 0.8-1.3, or 0.9-1.2 equivalents. In one embodiment, the ratio is 0.9-1.2 equivalents. In a preferred embodiment, the ratio is 0.9 equivalents.

The ratio (vol/vol) of the amount of the solvent and the amount of 5,6-dihydro-4H-pyrrolo[3,2,1-ij]quinolin-1-yl-oxoacetate can be 1-100, 3-90, 5-80, 10-70, 15-60, 20-50, or 30-40. In one embodiment, the ratio is 20-50. In a preferred embodiment, the ratio is 30-40. In a more preferred embodiment, the ratio is 37.

In a further embodiment, the base is dissolved or suspended in an organic solvent. In one embodiment, the base can be any base that is suitable for the reaction between 5,6-dihydro-4H-pyrrolo[3,2,1-ij]quinolin-1-yl-oxoacetate and indole-3-acetamide. For example, the base can be any base which can be used in the activation of active protons in the reaction. In one embodiment, the base is an inorganic base, including but not limited to, metal hydroxides such as sodium hydroxide, potassium hydroxide. In another embodiment, the base is a metal base, including but not limited to, metal alkoxides such as potassium tert-butoxide, sodium tert-butoxide, lithium hexamethyldisilazide, sodium hexamethyldisilazide, and lithium diisopropylamide. In a preferred embodiment, the base is metal alkoxides. In a more preferred embodiment, the base is potassium tert-butoxide. In one embodiment, the solvent can be any solvent which dissolves or suspends the base. In a further embodiment, the solvent is the same as the solvent used for dissolving methyl 5,6-dihydro-4H-pyrrolo[3,2,1-ij]quinolin-1-yl-oxoacetate and indole-3-acetamide. For example, the solvent is an ether, including but not limited to, dimethyl ether, diethyl ether, and THF, or a hydrocarbon, including but not limited to, toluene and hexane, or an amide, including but not limited to, DMF and dimethylacetamide. In a preferred embodiment, the solvent is an ether. In a more preferred embodiment, the solvent is THF.

The ratio of the amount of the base and the amount of 5,6-dihydro-4H-pyrrolo[3,2,1-ij]quinolin-1-yl-oxoacetate can be 1.0-10, 1.2-9.0, 1.4-8.0, 1.6-7.0, 1.8-6.0, 1.8-5.0, 1.8-4.0, 1.8-3.0, 1.9-2.5, or 2.0-2.2 equivalents. In one embodiment, the ratio is 2.0-2.2 equivalents. In a preferred embodiment, the ratio is 2.1 equivalents.

The solution containing methyl 5,6-dihydro-4H-pyrrolo[3,2,1-ij]quinolin-1-yl-oxoacetate and indole-3-acetamide can be added to the base in any manner. For example, the solution can be added to the base dropwise until all the solution is added. For example, the solution can be added to the base in less than 30 min, 20 min, 15 min, 10 min, 5 min, 2 min, or 1 min. For example, the solution can be added to the base for a duration of 0.5-12 hrs, 0.6-10 hrs, 0.75-8 hrs, 1-6 hrs, 1.5-5 hrs, or 2-4 hrs. For example, the solution can be added to the base with or without mixing. For example, the solution can be added to the base at any suitable temperature (e.g., 10-65° C., 20-65° C., and 45-55° C.).

The temperature of the reaction between 5,6-dihydro-4H-pyrrolo[3,2,1-ij]quinolin-1-yl-oxoacetate and indole-3-acetamide can be 0° C., 5° C., 10° C., 15° C., 20° C., 25° C., 30° C., 35° C., 40° C., 45° C., or 50° C., 55° C., or 60° C. above the reflux temperature of the solvent (e.g., THF). In one embodiment, the temperature is 10-65° C., 20-65° C., or 45-55° C. In a preferred embodiment, the temperature is 50-67° C.

The duration of the reaction between 5,6-dihydro-4H-pyrrolo[3,2,1-ij]quinolin-1-yl-oxoacetate and indole-3-acetamide can be 0.1-6 hrs, 0.25-5 hrs, or 0.5-2 hrs. In one embodiment, the duration of the reaction is 0.5 to 2 hrs.

In a further embodiment, highly pure 3-(5,6-dihydro-4H-pyrrolo[3,2,1-ij]quinolin-1-yl)-4-(1H-indol-3-yl)-1H-pyrrolidine-2,5-dione is formed by reducing 3-(5,6-dihydro-4H-pyrrolo[3,2,1-ij]quinolin-1-yl)-4-(1H-indol-3-yl)-1H-pyrrole-2,5-dione.

In one embodiment, the reduction of 3-(5,6-dihydro-4H-pyrrolo[3,2,1-ij]quinolin-1-yl)-4-(1H-indol-3-yl)-1H-pyrrole-2,5-dione to 3-(5,6-dihydro-4H-pyrrolo[3,2,1-ij]quinolin-1-yl)-4-(1H-indol-3-yl)-1H-pyrrolidine-2,5-dione is through hydrogenation. In one embodiment, the hydrogenation is conducted in the presence of palladium catalyst and a base. In one embodiment, the 3-(5,6-dihydro-4H-pyrrolo[3,2,1-ij]quinolin-1-yl)-4-(1H-indol-3-yl)-1H-pyrrolidine-2,5-dione produced is a cis-racemate. In a further embodiment, the cis-racemate is converted to a trans-racemate.

The palladium catalyst can be any palladium catalyst used in hydrogenation reaction. For example, the palladium catalyst is palladium hydroxide or palladium on a supporting material including but not limited to carbon, zeolite and alumina. In a preferred embodiment, the palladium catalyst is 5% palladium on carbon.

The ratio (w/w) of the amount of the palladium and the amount of 3-(5,6-dihydro-4H-pyrrolo[3,2,1-ij]quinolin-1-yl)-4-(1H-indol-3-yl)-1H-pyrrole-2,5-dione can be 0.05-0.5%, 0.06-0.4%, 0.07-0.3%, 0.08-0.2%, 0.09-0.15%, or 0.09-0.12%. In a preferred embodiment, the ratio is 0.09-0.12%. In a more preferred embodiment, the ratio is 0.1%.

The base can be any base suitable for use in the hydrogenation reaction. For example, the base is alkali metal alkoxides, including but not limited to potassium tert-butoxide, sodium tert-butoxide, and sodium methoxide, or alkali metal hydroxides, including but not limited to, potassium hydroxide and sodium hydroxide. In one embodiment, the base is alkali metal alkoxides. In a preferred embodiment, the base is potassium tert-butoxide.

The ratio of the amount of the base and the amount of 3-(5,6-dihydro-4H-pyrrolo[3,2,1-ij]quinolin-1-yl)-4-(1H-indol-3-yl)-1H-pyrrole-2,5-dione can be 0.1-2.0, 0.12-1.5, 0.14-1.0, 0.16-0.7, 0.18-0.5, or 0.19-0.3 equivalents. In one embodiment, the ratio is 0.19-0.3 equivalents. In a preferred embodiment, the ratio is 0.2 equivalents.

The solvent can be any solvent which dissolves 3-(5,6-dihydro-4H-pyrrolo[3,2,1-ij]quinolin-1-yl)-4-(1H-indol-3-yl)-1H-pyrrole-2,5-dione. In one embodiment, the solvent is an ether, including but not limited to, dimethyl ether, diethyl ether, and THF, or an alcohol, including but not limited to, methanol. In a preferred embodiment, the solvent is an ether. In a more preferred embodiment, the solvent is THF.

The pressure of hydrogen gas used in the hydrogenation reaction is preferably 0.3 to 5 MPa, more preferably 0.4 to 4 MPa.

The temperature of the hydrogenation reaction can be 5-100° C., 10-90° C., 20-80° C., 30-70° C., or 40-65° C. In a preferred embodiment, the temperature is 40-65° C. In a more preferred embodiment, the temperature is 55-65° C.

The duration of the hydrogenation reaction can be 1-48 hrs, 2-24 hrs, 3-16 hrs, or 4-10 hrs. In one embodiment, the duration is 4-10 hrs.

The methods for preparing highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof, of the present invention may further comprise a step of reacting 5,6-dihydro-4H-pyrrolo[3,2,1-ij]quinoline (lilolidine) with oxalyl chloride in a solvent and adding methanol thereto to produce 5,6-dihydro-4H-pyrrolo[3,2,1-ij]quinolin-1-yl-oxoacetate.

The amount of oxalyl chloride used in this step with respect to lilolidine is preferably 1.0 to 1.2 equivalents, more preferably 1.05 equivalents. The ratio (vol/vol) of the amount of the solvent used in this step with respect to the amount of lilolidine is preferably 10 to 30 times, more preferably 17 times. The amount of methanol used in this step with respect to lilolidine is preferably 2 to 20 equivalents, more preferably 6 equivalents.

The solvent used in this step can be any solvent which dissolves lilolidine to some extent and does not impair the reaction. For example, the solvent is an inert solvent. For example, the solvent can be ethers, including but not limited to, methyl tert-butyl ether, diethyl ether, diisopropyl ether, and THF, or hydrocarbons, including but not limited to toluene and hexane, or halogenated solvents, including but not limited to, dichloromethane and chloroform, or amide solvents, including but not limited to, dimethylformamide and dimethylacetamide. In one embodiment, the solvent is an ether. In a more preferred embodiment, the solvent is methyl tert-butyl ether or THF.

In this step, the reaction temperature at which methanol is added is preferably 5 to 50° C., more preferably 15 to 35° C. In this step, the reaction temperature is preferably 5 to 50° C., more preferably 15 to 35° C. The reaction time is preferably 5 minutes to 5 hours, more preferably 15 minutes to 1 hour.

The methods for preparing highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof, of the present invention may further comprise a step of producing a salt of the optically active (3R,4R)-3-(5,6-dihydro-4H-pyrrolo[3,2,1-ij]quinolin-1-yl)-4-(1H-indol-3-yl)-1H-pyrrolidine-2,5-dione from the trans-racemate of 3-(5,6-dihydro-4H-pyrrolo[3,2,1-ij]quinolin-1-yl)-4-(1H-indol-3-yl)-1H-pyrrolidine-2,5-dione through dynamic kinetic resolution in a solvent. The salt of (3R,4R)-3-(5,6-dihydro-4H-pyrrolo[3,2,1-ij]quinolin-1-yl)-4-(1H-indol-3-yl)-1H-pyrrolidine-2,5-dione is deposited as crystals, while the more soluble (3S,4S)-3-(5,6-dihydro-4H-pyrrolo[3,2,1-ij]quinolin-1-yl)-4-(1H-indol-3-yl)-1H-pyrrolidine-2,5-dione can be racemized with a base to produce the racemic mixture of 3-(5,6-dihydro-4H-pyrrolo[3,2,1-ij]quinolin-1-yl)-4-(1H-indol-3-yl)-1H-pyrrolidine-2,5-dione.

In one embodiment, (1S,2S)-(+)-pseudoephedrine, (R)-(−)-cyclohexylethylamine, (1S,2S)-2-methylaminocyclohexanol, (1S,2S)-2-(benzylamino)cyclopentanol, (1S,2R)-ephedrine, or (1R,2S)-(−)-norephedrine is used to produce the salt of the optically active 3-(5,6-dihydro-4H-pyrrolo[3,2,1-ij]quinolin-1-yl)-4-(1H-indol-3-yl)-1H-pyrrolidine-2,5-dione (e.g., (1S,2S)-3-(5,6-dihydro-4H-pyrrolo[3,2,1-ij]quinolin-1-yl)-4-(1H-indol-3-yl)-1H-pyrrolidine-2,5-dione). In a preferred embodiment, (1S,2S)-(+)-pseudoephedrine is used.

The salt of the optically active 3-(5,6-dihydro-4H-pyrrolo[3,2,1-ij]quinolin-1-yl)-4-(1H-indol-3-yl)-1H-pyrrolidine-2,5-dione may be further converted to a free form using an acid such as hydrochloric acid.

The solvent used in this step can be any solvent which dissolves the racemate of 3-(5,6-dihydro-4H-pyrrolo[3,2,1-ij]quinolin-1-yl)-4-(1H-indol-3-yl)-1H-pyrrolidine-2,5-dione and (3S,4S)-3-(5,6-dihydro-4H-pyrrolo[3,2,1-ij]quinolin-1-yl)-4-(1H-indol-3-yl)-1H-pyrrolidine-2,5-dione to some extent and has solubility at which the salt of (3R,4R)-3-(5,6-dihydro-4H-pyrrolo[3,2,1-ij]quinolin-1-yl)-4-(1H-indol-3-yl)-1H-pyrrolidine-2,5-dione (e.g., a mono-(1S,2S)-pseudoephedrine salt) can be crystallized. For example, the solvent can be an inert solvent. For example, the solvent can be ethers, including but not limited to, THF, or alcohols, including but not limited to, methanol and ethanol or an aqueous solution thereof. In one embodiment, the solvent is an alcohol. In a preferred embodiment, the solvent is methanol and ethanol. In a more preferred embodiment, the solvent is methanol.

The ratio (vol/vol) of the amount of the solvent used in this step with respect to the amount of 3-(5,6-dihydro-4H-pyrrolo[3,2,1-ij]quinolin-1-yl)-4-(1H-indol-3-yl)-1H-pyrrolidine-2,5-dione is preferably 7 to 15 times, more preferably 10 times. The amount of the base used in this step with respect to 3-(5,6-dihydro-4H-pyrrolo[3,2,1-ij]quinolin-1-yl)-4-(1H-indol-3-yl)-1H-pyrrolidine-2,5-dione is preferably 0.05 to 0.2 equivalents, more preferably 0.1 equivalents.

The base can be any base suitable for conducting the reaction. For example, the base can be alkali metal alkoxides, including but not limited to, sodium methoxide, sodium ethoxide and potassium tert-butoxide, or amines, including but not limited to, diazabicycloundecene. In one embodiment, the base is alkali metal alkoxides. In a preferred embodiment, the base is sodium methoxide.

The reaction temperature in this step is preferably 50 to 65° C., more preferably 50° C. The reaction time is preferably 12 to 48 hours, more preferably 16 hours.

The compound of the present invention can be purified by a usual method such as column chromatography or recrystallization. Particularly, the compound of the present invention can be purified by recrystallization from an alcohol, including but not limited to methanol.

3. Pharmaceutical Compositions

The present invention also relates to a pharmaceutical composition comprising the highly pure pyrroloquinolinyl-pyrrole-2,5-dione and pyrroloquinolinyl-pyrrolidine-2,5-dione, and pharmaceutically acceptable salts, solvates, diastereomers, and polymorphs thereof; and a pharmaceutically acceptable carrier.

The compound of the present invention, or pharmaceutically acceptable salts, solvates, diastereomers, and polymorphs thereof, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect, the compound of the present invention, or pharmaceutically acceptable salts, solvates, diastereomers, and polymorphs thereof; is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of the compound of the present invention, or pharmaceutically acceptable salts, solvates, diastereomers, and polymorphs thereof (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

4. Methods of Treatment

In one aspect, the compound of present invention, or pharmaceutically acceptable salts, solvates, diastereomers, and polymorphs thereof, modulates the activity of a molecular target (e.g., c-Met). In one aspect, modulating refers to stimulating or inhibiting an activity of a molecular target. Preferably, the compound of present invention, or pharmaceutically acceptable salts, solvates, diastereomers, and polymorphs thereof modulates the activity of a molecular target if it stimulates or inhibits the activity of the molecular target by at least 2-fold relative to the activity of the molecular target under the same conditions but lacking only the presence of said compound. More preferably, the compound of present invention, or pharmaceutically acceptable salts, solvates, diastereomers, and polymorphs thereof modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In one aspect, the compound of present invention, or pharmaceutically acceptable salts, solvates, diastereomers, and polymorphs thereof, does not significantly modulate the activity of a molecular target if the addition of the compound does not stimulate or inhibit the activity of the molecular target by greater than 10% relative to the activity of the molecular target under the same conditions but lacking only the presence of said compound.

In a preferred embodiment, administering the compound of present invention, or pharmaceutically acceptable salts, solvates, diastereomers, and polymorphs thereof, to a cell or a subject in need thereof results in modulation (i.e., stimulation or inhibition) of an activity of c-Met. As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK. c-Met knockdown has been shown to inhibit cancer cell growth in a cell-type-specific manner. MDA-MB-231, NCI-H661, NCI-H441, MIA PaCa-2, HT29 and MKN-45 human cancer cells. c-Met knockdown induces caspase-dependent apoptosis in a cell type-specific manner. Thus, the present invention is directed to the treatment of cell proliferative disorders where the cells express c-Met at high levels or express active c-Met.

In one aspect, activating refers to placing a composition of matter (e.g., protein or nucleic acid) in a state suitable for carrying out a desired biological function. In one aspect, a composition of matter capable of being activated also has an inactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter.

In a preferred aspect, an effective amount of the compound of present invention, or pharmaceutically acceptable salts, solvates, diastereomers, and polymorphs thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

In one aspect, contacting a cell with the compound of present invention, or pharmaceutically acceptable salts, solvates, diastereomers, and polymorphs thereof, induces or activates cell death selectively in cancer cells. Preferably, administering to a subject in need thereof the compound of present invention, or pharmaceutically acceptable salts, solvates, diastereomers, and polymorphs thereof, induces or activates cell death selectively in cancer cells. In another aspect, contacting a cell with the compound of present invention, or pharmaceutically acceptable salts, solvates, diastereomers, and polymorphs thereof, induces cell death selectively in one or more cells affected by a cell proliferative disorder.

In a preferred aspect, the present invention relates to a method of treating or preventing cancer by administering the compound of present invention, or pharmaceutically acceptable salts, solvates, diastereomers, and polymorphs thereof to a subject in need thereof, where administration of the compound of present invention, or pharmaceutically acceptable salts, solvates, diastereomers, and polymorphs thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., 18th edition (1990). These texts can, of course, also be referred to in making or using an aspect of the invention.

5. Definitions

All stereoisomers of the compounds of the instant invention are contemplated, either in admixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, alkylsulphonate, arylsulphonate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, e.g., Berge et al. (1977) "Pharmaceutical Salts", *J. Farm. SCI.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances include relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

As used herein, the term "metabolite" means a product of metabolism of the compound of present invention, or pharmaceutically acceptable salts, solvates, diastereomers, and polymorphs thereof, that exhibits a similar activity in vivo to the compound of present invention, or pharmaceutically acceptable salts, solvates, diastereomers, and polymorphs thereof.

As used herein, the term "prodrug" means the compound of present invention, or pharmaceutically acceptable salts, solvates, diastereomers, and polymorphs thereof covalently linked to one or more pro-moieties, such as an amino acid moiety or other water solubilizing moiety. The compound of present invention, or pharmaceutically acceptable salts, solvates, diastereomers, and polymorphs thereof may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake. Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; and Greene, T. W., Wuts, P. G. M., *Protective Groups in Organic Synthesis,* 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of the present invention may be prepared according to the following schemes and examples from commercially available starting materials or starting materials which can be prepared using literature procedures. These procedures show the preparation of representative compounds of the present invention.

6. EXAMPLES

Examples are provided below to further illustrate different features of the present invention. The examples also illustrate useful methodology for practicing the invention. These examples do not limit the claimed invention.

Example 1

Synthesis Scheme

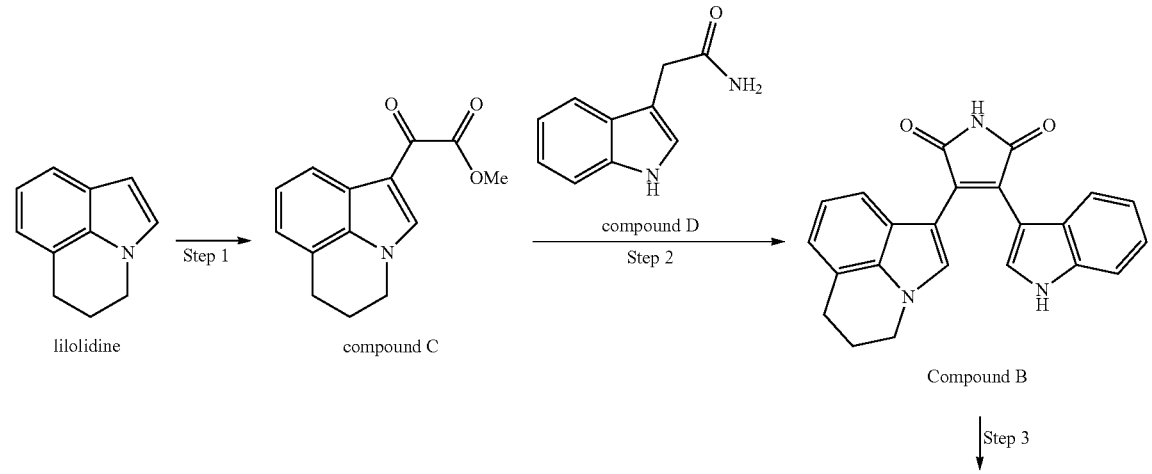

Step 3

-continued

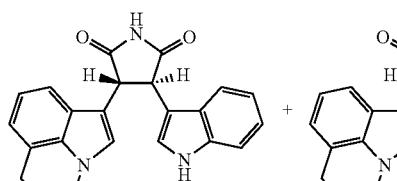

compound A (trans racemate)

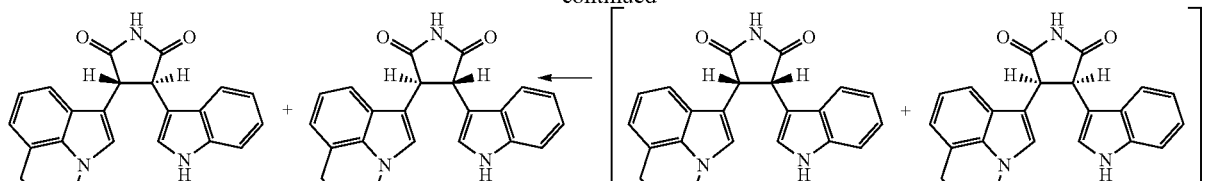

compound A (cis racemate)

↓ Step 4

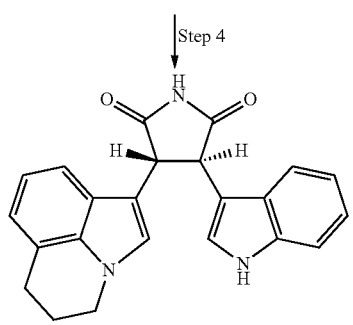

(3R,4R)-compound A complex

Step 5 →

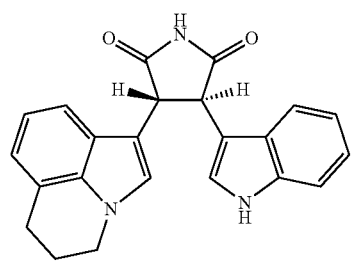

(3R,4R)-compound A

Both of methyl 5,6-dihydro-4H-pyrrolo[3,2,1-ij]quinolin-1-yl-oxoacetate (compound C) and indole-3-acetamide (compound D), are compounds known in the art and can be prepared by a method described, for example, in PCT Publication No. WO2006/004456.

Step 1: synthesis of methyl 5,6-dihydro-4H-pyrrolo[3,2,1-ij]quinolin-1-yl-oxoacetate (compound C)

In one aspect, Step 1 is the reaction of lilolidine with oxalyl chloride in an inert solvent and methanol to form compound C. In one aspect, the amount of oxalyl chloride used with respect to lilolidine is about 1.0 to about 1.2 equivalents. In another aspect, the amount of oxalyl chloride to lilolidine is about 1.05 equivalents.

The inert solvent used in Step 1 is not particularly limited as long as it dissolves the raw material lilolidine to some extent and does not impair the reaction. In one aspect, the inert solvent is an ether selected from methyl tert-butyl ether, diethyl ether, diisopropyl ether, and tetrahydrofuran. In another aspect, the ether is methyl tert-butyl ether. In another aspect, the ether is tetrahydrofuran. In another aspect, the inert solvent is a hydrocarbon selected from toluene and hexane. In another aspect, the inert solvent is a halogenated solvent selected from dichloromethane and chloroform. In another aspect, the inert solvent is an amide solvent selected from dimethylformamide and dimethylacetamide. In one aspect, the volume ratio of the inert solvent used in Step 1 with respect to lilolidine is about 10 to 30 times. In one aspect, the volume ratio is about 17 times.

In one aspect, the reaction temperature at which lilolidine is reacted with oxalyl chloride is about 5° C. to about 50° C. In another aspect, the reaction temperature is about 15° C. to about 35° C. The reaction time is about 5 minutes to about 5 hours. In another aspect, the reaction time is about 15 minutes to 1 hour.

In one aspect, the amount of methanol used in Step 1 with respect to lilolidine is about 2 to about 20 equivalents. In another aspect, the amount of methanol to lilolidone is about 6.3 equivalents. In one aspect, the reaction temperature at which methanol is added is about 5° C. to about 50° C. In another aspect, the reaction temperature is about 15° C. to 35° C. In another aspect, the reaction time is about 5 minutes to about 5 hours. In another aspect, the reaction time is about 15 minutes to 1 hour.

Compound C obtained in Step 1 can be used in Step 2 without further purification.

Step 2: cyclization reaction of compound C and indole-3-acetamide (compound D) to form 3-(5,6-dihydro-4H-pyrrolo[3,2,1-ij]quinolin-1-yl)-4-(1H-indol-3-yl)-1H-pyrrole-2,5-dione (compound B)

In one aspect, Step 2 is the reaction of compound C with compound D in the presence of a base in an inert solvent to form compound B. The amount of compound D used with respect to compound C is about 0.9 to about 1.2 equivalents. In one aspect, the amount of compound D to compound C is about 0.9 equivalents.

The inert solvent used in this step is not particularly limited as long as it dissolves the compounds C and D to some extent and does not impair the reaction. In one aspect, the inert solvent is an ether selected from diethyl ether and THF. In one aspect, the inert solvent is diethyl ether. In another aspect, the insert solvent is THF. In another aspect, the inert solvent is a hydrocarbon selected from toluene and hexane. In another aspect, the inert solvent is an amide solvent selected from dimethylformamide and dimethylacetamide. The volume ratio of the solvent used with respect to compound C is about 15 to about 60 times. In one aspect, the volume ratio is about 37 times.

The base used in this step is not particularly limited as long as it is a base used in the activation of active protons. In one aspect, the base an alkali metal alkoxide. In one aspect, the alkali metal alkoxide is potassium tert-butoxide. In another aspect, the base is metal bases. In one aspect, the metal base is selected from hexamethyldisilazane and lithium diisopropylamide. The amount of the base used with respect to compound C is about 2.0 to about 5.0 equivalents. In one aspect, the amount of base to compound C is about 2.1 equivalents.

The reaction temperature is about 15° C. to the reflux temperature of the inert solvent. In one aspect, the reaction temperature is about 45° C. to about 55° C. The reaction time is about 0.25 hour to about 6 hours. In another aspect, the reaction time is about 0.5 to 2 hours.

Compound B obtained in this step can be purified by a known method. In one aspect, compound B is washed with an organic solvent such as methylene chloride or heptane. In another aspect, compound B is washed with an alcohol or an aqueous solution thereof; such as ethanol or aqueous ethanol.

Step 3: reduction of compound B to form 3-(5,6-dihydro-4H-pyrrolo[3,2,1-ij]quinolin-1-yl)-4-(1H-indol-3-yl)pyrrolidine-2,5-dione (compound A)

In one aspect, Step 3 is the conversion of compound B to compound A. In one aspect, the conversion comprises of reacting compound B with a catalyst and $H_2$ in the presence of an organic solvent. In one aspect, the catalyst is a palladium catalyst. In another aspect, the catalyst is selected from Pd/C and Pd(OH)$_2$/C. In one aspect, the catalyst is Pd/C. In another aspect, the catalyst is 5% Pd/C. The amount of the palladium catalyst used with respect to compound B is about 0.05% to about 0.5% by weight. In another aspect, the amount of palladium catalyst to compound B is about 0.1% by weight (in terms of dry weight).

In one aspect, the organic solvent is a polar aprotic solvent. In another aspect, the polar aprotic solvent is tetrahydrofuran. In one aspect, the conversion of compound B to compound A further comprises of a base. In one aspect, the base is potassium tert-butoxide. In one aspect, compound A (cis racemate) is formed. In another aspect, compound A (cis racemate) is further converted to compound (trans racemate). In one aspect, it is not required to isolate compound (cis racemate).

The inert solvent used in this step is not particularly limited as long as it dissolves compound B to some extent and does not impair the reaction. In one aspect, the inert solvent is an ether; in one aspect, the ether is THF. In another aspect, the inert solvent is an alcohol; in one aspect, the alcohol is methanol. The volume ratio of the inert solvent used with respect to compound B is about 10 to about 30 times. In one aspect, the volume ratio is about 20 times.

The base used in this step is not particularly limited as long as it has the predetermined basicity. In one aspect, the base is an alkali metal alkoxide; in one aspect, the alkali metal alkoxide is selected from potassium tert-butoxide and sodium methoxide; in one aspect, the alkali metal alkoxide is potassium tert-butoxide. In another aspect, the base is an alkali metal hydroxide; in another aspect, the alkali metal hydroxide is selected from potassium hydroxide and sodium hydroxide. The amount of the base used with respect to compound B is about 0.1 to about 2.0 equivalents. In one aspect, the amount of base to compound B is about 0.2 equivalents.

The pressure of hydrogen gas used is about 0.3 MPa to about 1.0 MPa. In one aspect, the pressure is about 0.4 to 0.5 MPa. The temperature of the reaction mixture is about 40° C. to 65° C. In another aspect, the temperature is about 55 to 65° C. In one aspect, the reaction time is about 4 hours to about 10 hours.

In one aspect, compound A (trans racemate) obtained in this step is purified before Step 4. In one aspect, compound A (trans racemate) is purified by a known method such as column chromatography or recrystallization.

Step 4: conversion of compound A to a (3R,4R)-compound A complex

In one aspect, Step 4 is the conversion of compound A (trans racemate) in an inert solvent to form a (3R,4R)-compound A complex. In one aspect, compound A (trans racemate) is reacted with a compound is selected from (1S,2S)-(+)-pseudoephedrine, (R)-(−)-cyclohexylethylamine, (1S,2S)-2-methylaminocyclohexanol, (1S,2S)-2-(benzylamino)cyclopentanol, (1S,2R)-ephedrine, and (1R,2S)-(−)-norephedrine. In one aspect, the compound is (1S,2S)-(+)-pseudoephedrine. In one aspect, the (3R,4R)-compound A complex is the (3R,4R)-compound A (1S,2S)-(+)-pseudoephedrine salt ((3R,4R)-compound A·PSE).

In one aspect, the inert solvent is an ether; in one aspect, the ether is THF. In one aspect, the inert solvent is an alcohol; in one aspect, the alcohol is methanol and ethanol or an aqueous solution thereof. In aspect, the alcohol is methanol. In another aspect, the inert solvent is an inert solvent that dissolves the compound A (trans racemate) and (3S,4S)-compound A complex some extent and has the degree of dissolution at which (3R,4R)-compound A complex is deposited as crystals. The volume ratio of the inert solvent respect to compound A (trans racemate) is about 7 to about 15 times. In another aspect, the volume ration is about 10 times.

In one aspect, reacting compound A (trans racemate) with a chiral compound in an inert solvent to form a (3R,4R)-compound A complex further comprise of a adding a base. The base used is not particularly limited as long as it has the predetermined basicity. In one aspect, the base is selected from alkali metal alkoxides; in one aspect, the alkali metal alkoxide is selected from sodium methoxide, sodium ethoxide and potassium tert-butoxide. In one aspect, the alkali metal alkoxide is sodium methoxide. In another aspect, the base is an amine; in one aspect, the amine is diazabicycloundecene. The amount of the base with respect to compound A (trans racemate) is about 0.05 to about 0.2 equivalents. In one aspect, the amount of base to compound A (trans racemate) is about 0.1 equivalents.

The temperature of the reaction mixture is about 50° C. to 65° C. In one aspect, the temperature is about 50° C. The reaction time is about 12 hours to about 48 hours. In one aspect, the reaction time is about preferably 16 hours.

In one aspect, the (3R,4R)-compound A complex is (3R,4R)-compound A·PSE. In one aspect, the (3R,4R)-compound A·PSE obtained in this step can be used in Step 5 without being dried.

Step 5: conversion of the (3R,4R)-compound A complex to (3R,4R)-compound A

In one aspect, Step 5 is the conversion of (3R,4R)-compound A complex to (3R,4R)-compound. In one aspect, Step 4 is the conversion of (3R,4R)-compound A·PSE in the presence of an acid and an inert solvent to (3R,4R)-compound A. The inert solvent used is not particularly limited as long as it dissolves to some extent (3R,4R)-compound A complex and does not impair the reaction. In one aspect, the inert solvent is an ether; in one aspect, the ether is THF. In another aspect, the inert solvent is an alcohol or an aqueous solution thereof; in one aspect, the alcohol is methanol or aqueous methanol. The acid used is not particularly limited as long as it has the predetermined acidity. In one aspect, the acid is selected from hydrochloric acid, sulfuric acid, phosphoric acid, trifluoroacetic acid, and acetic acid. In one aspect, the acid is hydrochloric acid.

Example 2

Yield and Purity of the Compounds of the Present Invention

The method of present invention is advantageous as compared to methods known in the art, such as those described in PCT publication WO2006/086484 and WO2011/079142. Particularly, the methods of the present application offer substantial improvements related to scale-up optimization as well as purity and improvements in the overall process. For example, (3R,4R)-compound A is prepared in at least 52% overall yield in 99.9% purity according to present methods. On the contrary, the methods as previously described in WO2006/086484 and WO2011/079142 afford a 47% overall yield for (3R,4R)-compound A. In addition, the present methods produce substantially pure compound B and substantially pure compound A on a large scale. Specifically, the present methods produces substantially pure compound B in large amounts by adding compound C and compound D to a base.

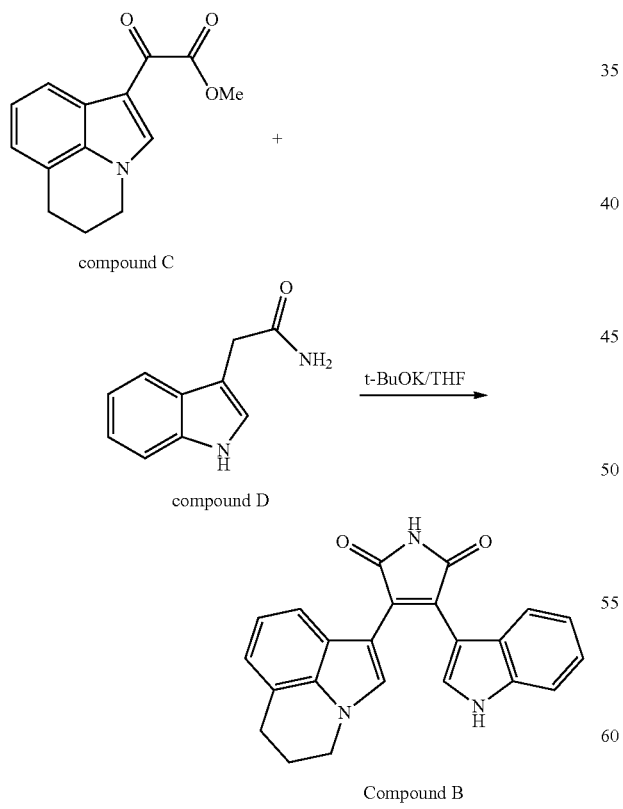

As a result of the purity of compound B, compound A prepared from such substantially pure compound B also has a substantially high purity.

Example 3

Preparation of (3R,4R)-3-(5,6-dihydro-4H-pyrrolo[3,2,1-ij]quinolin-1-yl)-4-(1H-indol-3-yl)pyrrolidine-2,5-dione ((3R,4R)-compound A)

Step 1: Preparation of methyl 2-(5,6-dihydro-4H-pyrrolo[3,2,1-ij]quinolin-1-yl)-2-oxoacetate

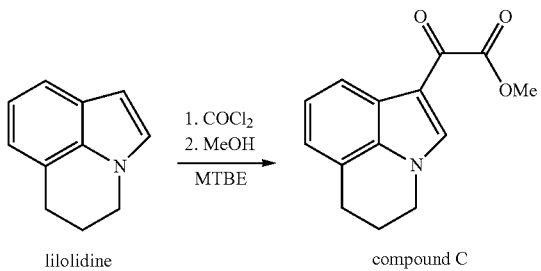 [SMILES: c1cc2c3c(c1)ccn3CCC2 ; COC(=O)C(=O)c1cn2c3c(cccc13)CCC2]

Lilolidine (5,6-dihydro-4H-pyrrolo[3,2,1-ij]quinoline, 105.0 g) was dissolved in tert-butyl methyl ether (MTBE, 1050 mL), and this solution was added dropwise to a solution of oxalyl chloride (62 mL) in MTBE (735 mL) at 32° C. or lower over about 1 hour under the nitrogen atmosphere. This solution was stirred at 20° C. to 30° C. for about 1 hour. Then, methanol (171 mL) was added, and the mixture was stirred at about 25° C. for about 1 hour. Then, the solution containing compound C was concentrated to about 525 mL by concentration under reduced pressure, and then, tetrahydrofuran (THF, 1575 mL) was added. The solution containing compound C was further concentrated to about 525 mL by concentration under reduced pressure, and then, THF (840 mL) was added. The solution containing compound C was concentrated again to 525 mL by concentration under reduced pressure to adjust the methanol concentration to about 1% by weight or less. This residue containing compound C was used in the next step without further purification.

Step 2: Preparation of 3-(5,6-dihydro-4H-pyrrolo[3,2,1-ij]quinolin-1-yl)-4-(1H-indol-3-yl)-1H-pyrrole-2,5-dione (compound B)

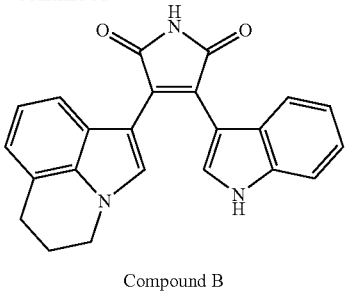

Compound B

To compound C, indole-3-acetamide (104.71 g) and THF (1428 mL) were added at about 15° C. to about 35° C. under a nitrogen atmosphere. The resulting solution was added dropwise in the range of about 20° C. to about 32° C. over about 30 minutes or longer under a nitrogen atmosphere to a 1 M solution of potassium tert-butoxide in THF (1382.5 mL) further diluted with THF (420 mL). The reaction solution was stirred at about 20° C. to about 32° C. for about 2 hours. Then, 12 M hydrochloric acid (312 mL) was added dropwise at about 50° C. or lower, and the mixture was stirred at about 40° C. to about 50° C. for about 1 hour. After the completion of reaction, water (465 mL) and 28% ammonia water (465 mL) were added to the reaction solution, and the mixture was stirred at about 20° C. to about 32° C. for about 30 minutes or longer and then separated into aqueous and organic layers. The aqueous layer was removed. The organic layers containing compound B were combined and concentrated to about 2100 mL under a reduced pressure at an internal temperature of about 60° C. or lower. Ethanol (4095 mL) was added to the concentrated solution containing compound B. The resulting solution containing compound B was further concentrated to about 2100 mL under a reduced pressure at about 60° C. or lower, and then, ethanol (1050 mL) was added. The solution was concentrated to about 2100 mL under a reduced pressure at about 60° C. or lower to adjust the THF concentration to 2% or less. The concentrated solution obtained was cooled to about 20° C. to about 30° C., and water (2100 mL) was added dropwise over about 1 hour or longer. The resulting mixture containing compound B was stirred at about 20° C. to about 30° C. for 1 hour. The deposited crystals of compound B were collected by filtration and washed with a 50% aqueous ethanol solution (1050 mL). The crystals of compound B were dried in vacuum at about 45° C. to about 55° C. for about 12 hours or longer (178.7 g, yield: 80.9% (calculated based on indole-3-acetamide)).

The crystals of compound B thus obtained can be used directly in next step. The crystals of compound B may be further purified as follows: methylene chloride (750 mL) was added to the crystals of compound B (150.0 g), and the mixture was stirred at about 15° C. to about 25° C. for about 2 hours or longer. To this suspension containing compound B, heptane (750 mL) was added dropwise at about 15° C. to about 25° C. over about 1 hour or longer, and the mixture was stirred at about 15° C. to about 25° C. for about 2 hours or longer. The deposited crystals of compound B were collected by filtration and washed with a mixed solvent of methylene chloride and heptane (mixing ratio: 1/1) (450 mL). The crystals of compound B were dried in vacuum at about 45° C. to about 55° C. for about 12 hours or longer (146.1 g, yield from crystals before purification: 97.4%).

Step 3: Preparation of (3RS,4RS)-3-(5,6-dihydro-4H-pyrrolo[3,2,1-ij]quinolin-1-yl)-4-(1H-indol-3-yl)pyrrolidine-2,5-dione (compound A (trans-racemate))

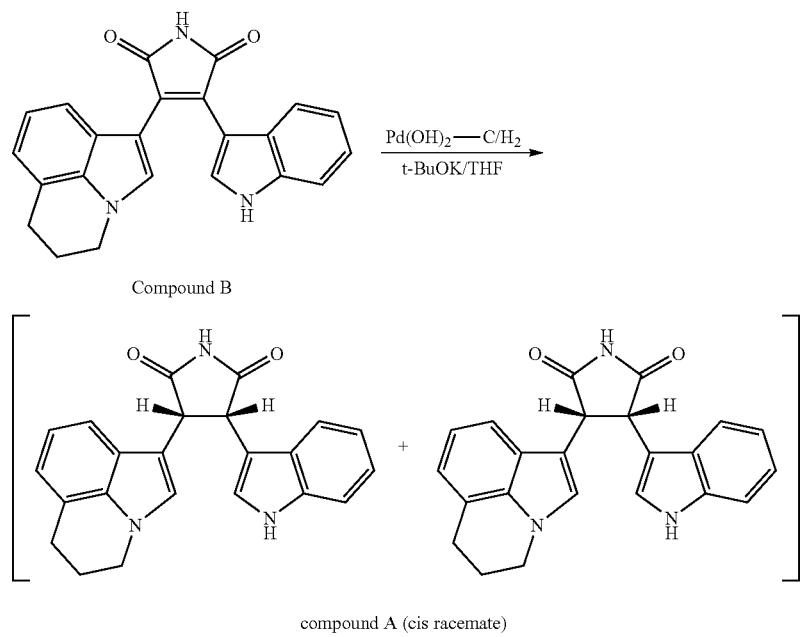

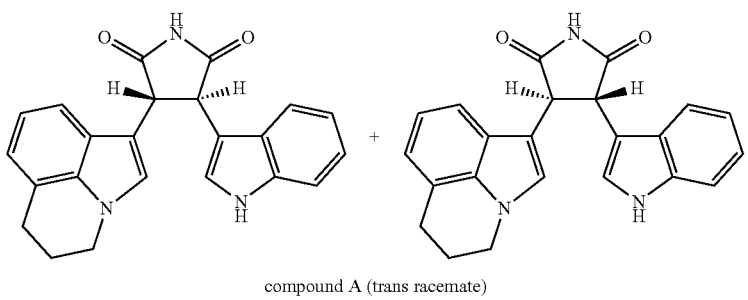

compound A (trans racemate)

THF (1200 mL) was added to 20% palladium (II) hydroxide-carbon (Pd(OH)$_2$—C, 50% wet product, 12.4 g (in terms of dry weight)), and the mixture was stirred at room temperature. The atmosphere of the mixture containing Pd(OH)$_2$—C was replaced by nitrogen gas to remove oxygen, and then, hydrogen gas was injected. The procedure of replacing the atmosphere with nitrogen gas and then injecting gas was repeated three times, and the reaction mixture was stirred at a hydrogen pressure (448 kPaG) at room temperature for about 3 hours or longer. To the Pd(OH)$_2$—C mixture, a solution of compound B (crystals obtained in Step 2, 120.0 g) in THF (1200 mL) was added at room temperature. Then, a 1 M solution of potassium tert-butoxide in THF (65.32 mL) was added dropwise. Then, oxygen in the reaction mixture was removed using nitrogen gas, and then, hydrogen gas was injected. The pressure was adjusted to a hydrogen pressure (448 kPaG) and the reaction mixture was stirred at about 45° C. to about 50° C. for about 12 hours or longer. After the completion of reaction, the reaction mixture was cooled to about 15° C. to about 25° C., and hydrogen in the system was removed using nitrogen gas. To remove the Pd-catalyst, the reaction mixture was filtered and washed with THF (600 mL). Isopropyl acetate (960 mL), water (480 mL), and 1 M hydrochloric acid (240 mL) were added to the filtrate containing compound A (trans-racemate), and the mixture was stirred at room temperature and then separated into aqueous and organic layers. The aqueous layer was removed, and the organic layer containing compound A (trans-racemate) was retained. Isopropyl acetate (240 mL) was added to the removed aqueous layer, and the mixture was stirred at room temperature and then separated into aqueous and organic layers. The aqueous layer was removed, and the organic layer containing compound A (trans-racemate) was retained. The organic layers containing compound A (trans-racemate) were combined. 1 M hydrochloric acid (360 mL) was added, and the mixture was stirred at room temperature and then separated into aqueous and organic layers. The aqueous layer was removed. To the organic layer containing compound A (trans-racemate), about 360 mL of a mixed solution of saturated saline and water (mixing ratio: 1/1) was added, and the mixture was separated into aqueous and organic layers at room temperature. The aqueous layer was removed. The obtained organic layer was concentrated to about 600 mL or less under a reduced pressure at an internal temperature of about 40° C. or lower, and isopropyl acetate (2040 mL) was added. The solution containing compound A (trans-racemate) was concentrated to 1800 mL or less under a reduced pressure at an internal temperature of about 40° C. or lower, and isopropyl acetate (1800 mL) was added. The solution containing compound A (trans-racemate) was concentrated to 1800 mL or less under a reduced pressure at an internal temperature of about 40° C. or lower to adjust the THF in the residue to about 0.1% or less. Then, heptane (3000 mL) was added dropwise at an internal temperature of about 15° C. to about 30° C. over about 30 minutes or longer. The resulting mixture was stirred at t about 15° C. to about 30° C. for about 1 hour or longer. Then, the deposited crystals of compound A (trans-racemate) were collected by filtration and washed with heptane (600 mL). The crystals compound A (trans-racemate) were dried in vacuum at about 50° C. for about 12 hours or longer (116.0 g, yield: 96.1%).

Step 4: Preparation of (3R,4R)-3-(5,6-dihydro-4H-pyrrolo[3,2,1-ij]quinolin-1-yl)-4-(1H-indol-3-yl)pyrrolidine-2,5-dione mono-(1S,2S)-pseudoephedrine (3R,4R-compound A·PSE)

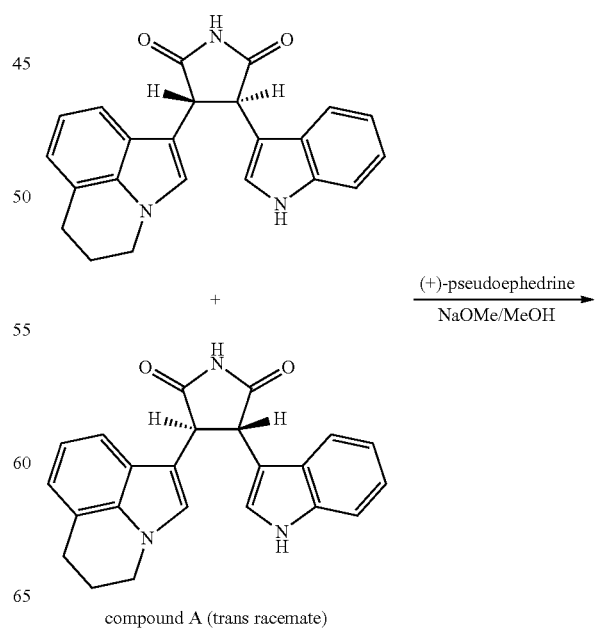

compound A (trans racemate)

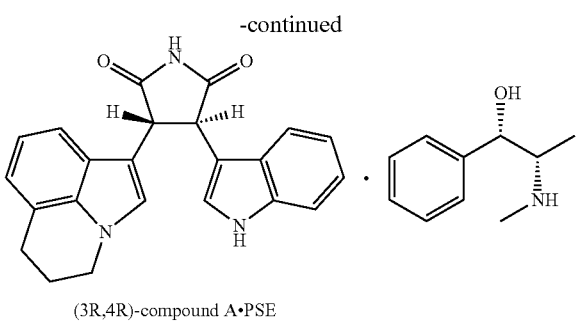

(3R,4R)-compound A·PSE

Methanol (415 mL) was added to the compound A (trans-racemate) (50.0 g) obtained in Step 3, and (1S,2S)-pseudoephedrine (22.3 g) was added at room temperature under a nitrogen atmosphere. The mixture was stirred at about 45° C. to about 55° C. for about 3 hours or longer. Then, sodium methoxide/methanol (2.8 mL) was added dropwise, and the reaction mixture was stirred at about 45° C. to about 55° C. for about 16 hours or longer. To the reaction mixture, a mixed solution of 1 M hydrochloric acid (12.4 mL) and water (29 mL) was added dropwise at about 45° C. to about 55° C., and the reaction mixture was stirred at about 45° C. to about 55° C. for about 1 hour. The reaction mixture was cooled to about 15° C. to about 25° C. and then stirred at about 15° C. to about 25° C. for about 2 hours. The deposited crystals of (3R,4R)-compound A·PSE were collected by filtration and washed with a 90% aqueous methanol solution (125 mL). The crystals of (3R,4R)-compound A·PSE were dried in vacuum at about 50° C. for about 12 hours (49.6 g, yield: 85.0%).

Step 5: Preparation of (3R,4R)-3-(5,6-dihydro-4H-pyrrolo[3,2,1-ij]quinolin-1-yl)-4-(1H-indol-3-yl)pyrrolidine-2,5-dione (3R,4R-compound A)

about 2 hours to about 3 hours. The reaction mixture was cooled to about 15° C. to about 25° C. over about 1 hour and then stirred at about 15° C. to about 25° C. for about 1 hour. The deposited crystals were filtered and washed with a about 50% aqueous methanol solution (80 mL). The crude crystals of (3R,4R)-compound A were dried in vacuum at about 50° C. for about 12 hours or longer (26.5 g, yield: 96.0%).

Step 6: Optional preparation of crystalline (3R,4R)-3-(5,6-dihydro-4H-pyrrolo[3,2,1-ij]quinolin-1-yl)-4-(1H-indol-3-yl)pyrrolidine-2,5-dione (3R,4R-compound A)

To the crude crystals of (3R,4R)-compound A (10.00 g), methanol (30 mL) and THF (15 mL) were added, and the crystals were dissolved at about 30° C. to about 35° C. under a nitrogen atmosphere. To the solution containing (3R,4R)-compound A, activated carbon (1.06 g) was added at about 30° C. to about 35° C., and the mixture was stirred for about 1 hour or longer. Activated carbon was filtered off, and the residue was washed with a mixed solution of methanol (13 mL) and THF (7 mL) (mixing ratio: 2/1). The obtained solution was combined with the washes, and the mixture was concentrated to about 50 mL at ambient pressure. To concentrated solution containing (3R,4R)-compound A, methanol (17 mL) was then added at about 57° C. to about 67° C. to adjust the THF concentration in the system to about 18% to about 20%. The solution containing (3R,4R)-compound A was adjusted to about 55° C. to about 65° C. Form-1 seed crystals of compound A (0.11 g) obtained by a method described in PCT Publication No. WO2011/079142 was added, and the mixture was stirred at to about 55° C. to about 65° C. for about 4 hours. Then, the solution containing (3R,4R)-compound A was concentrated to about 54 mL under ambient pressure, and methanol (40 mL) was added at about 57° C. to about 67° C. The solution containing (3R,4R)-

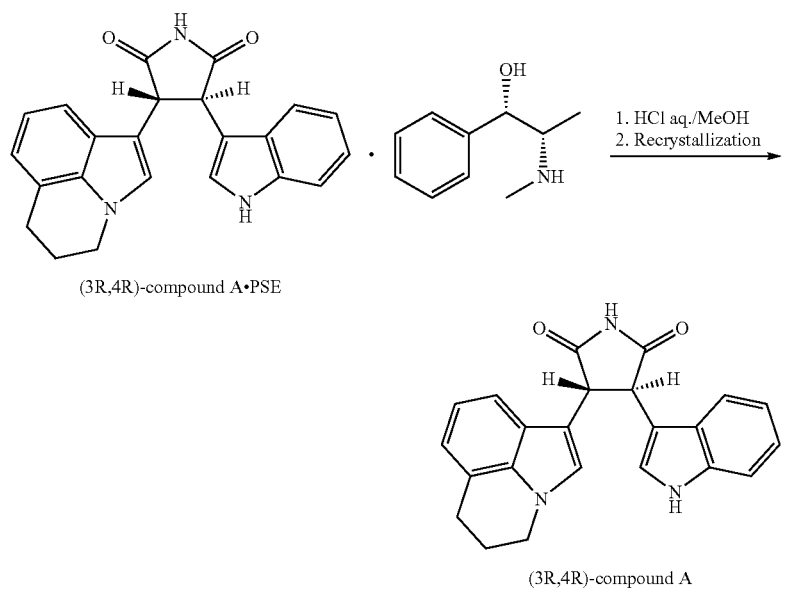

To (3R,4R)-compound A·PSE (40 g) obtained in step (3), water (160 mL), 1 M hydrochloric acid (82.3 mL), and methanol (240 mL) were added at room temperature, and the mixture was heated to about 45° C. to about 55° C. and stirred for compound A was concentrated to about 54 mL under ambient pressure at about 57° C. to about 67° C. The concentrated solution containing (3R,4R)-compound A was cooled to about 45° C. to about 55° C. and stirred at the same temperature as above for about 3 hours. Then, the reaction solution was cooled to about −5° C. to about 5° C. at a cooling rate of about 5° C./15 min and stirred at −5° C. to about 5° C. for about 3 hours. The deposited crystals of (3R,4R)-compound A were collected by filtration and washed with a mixed solution of methanol (12 mL) and water (3 mL) (mixing ratio: 4/1) at −5° C. to about 5° C. The crystals (3R,4R)-compound A were dried in vacuum at about 50° C. for about 6 hours or longer (8.57 g, yield from crude crystals: 85.7%, purity: >99.9%).

Example 4

Preparation of 3-(5,6-dihydro-4H-pyrrolo[3,2,1-ij]quinolin-1-yl)-4-(1H-indol-3-yl)-1H-pyrrole-2,5-dione (compound B)

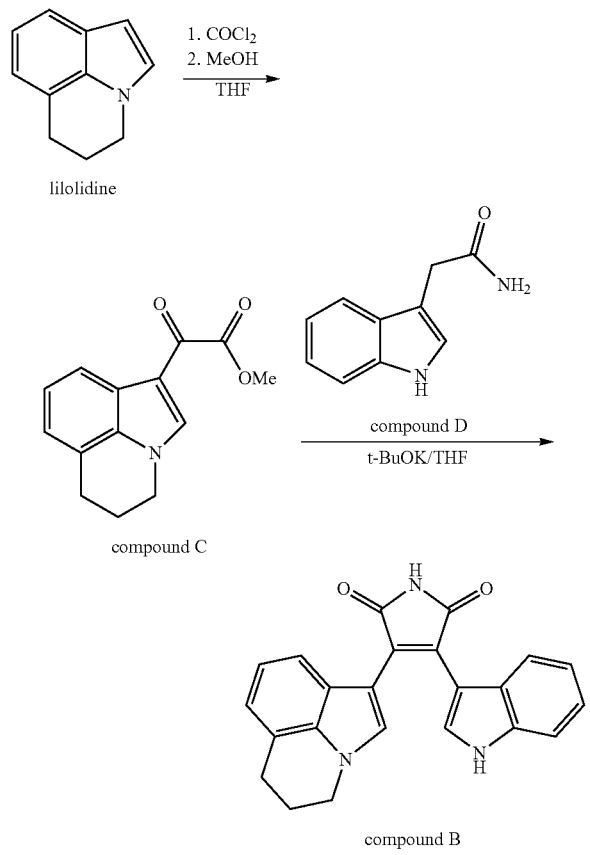

To a solution of oxalyl chloride (12.2 mL) in THF (70 mL), a solution of lilolidine (5,6-dihydro-4H-pyrrolo[3,2,1-ij]quinoline, 20.0 g) in THF (100 mL) was added dropwise at about 15° C. to about 35° C. over about 30 minutes under a nitrogen atmosphere. The reaction mixture was stirred at about 15° C. to about 35° C. for 15 minutes or longer. Then, methanol (8 mL) was added, and the reaction mixture was stirred at about 15° C. to about 35° C. for about 15 minutes or longer. To this reaction mixture, indole-3-acetamide (20.0 g) and THF (200 mL) were added, and the reaction mixture was heated to about 35° C. to about 45° C. The reaction mixture was added dropwise at about 45° C. to about 65° C. over about 30 minutes under a nitrogen atmosphere to a solution of potassium tert-butoxide (60.0 g) in THF (200 mL), which was heated in advance at about 45° C. to about 55° C. The reaction mixture was stirred at about 45° C. to about 55° C. for about 30 minutes or longer. Then, 12 M hydrochloric acid (30.0 mL) was added dropwise, and the reaction mixture was stirred at about 45° C. to about 65° C. for about 30 minutes or longer. Water (150 mL) and about 28% ammonia water (50 mL) were added, and the mixture was stirred at 45° C. to about 65° C. for about 15 minutes or longer and then separated into aqueous and organic layers. The aqueous layer was removed. The organic layer containing compound B was concentrated to about 200 mL under a reduced pressure at an internal temperature of about 60° C. or lower. To concentrated solution containing compound B, ethanol (400 mL) was added. The resulting solution was further concentrated to about 200 mL under a reduced pressure at about 60° C. or lower, and then, ethanol (400 mL) was added. The resulting solution was concentrated again to about 200 mL by concentration under a reduced pressure at about 60° C. or lower, and then, ethanol (200 mL) was added. The resulting solution containing compound B was stirred at about 55° C. to about 65° C. for about 1 hour, and then, water (400 mL) was added dropwise over 1 hour or longer. The resulting mixture containing compound B was stirred at about 55° C. to about 65° C. for about 1 hour. Then, the deposited crystals of compound B were collected by filtration and washed with a 50% aqueous ethanol solution (500 mL). The crystals of compound B were dried in vacuum at about 45° C. to about 55° C. for about 12 hours or longer (35.5 g, yield: 84.4% (calculated based on indole-3-acetamide)).

The crystals of compound B thus obtained can be used directly in next step. The crystals of compound B can also be purified as follows: ethanol (50 mL) was added to the crystals of compound B (10.0 g), and the resulting mixture was stirred at about 55° C. to about 65° C. for about 1 hour or longer. To this suspension, water (25 mL) was added dropwise at about 55° C. to about 65° C. over about 1 hour or longer, and the resulting mixture was stirred at about 55° C. to about 65° C. for about 1 hour or longer. Then, the reaction mixture was cooled to about 20° C. to about 30° C. over about 1 hour or longer and stirred at about 20° C. to about 30° C. for about 1 hour or longer. The deposited crystals of compound B were collected by filtration and washed with a mixed solvent of ethanol and water (mixing ratio: 2/1) (15 mL). The crystals of compound B were dried in vacuum at about 45° C. to about 55° C. for about 12 hours or longer (9.50 g, yield from crystals before purification: 95.0%).

Example 5

Preparation of (3RS,4RS)-3-(5,6-dihydro-4H-pyrrolo[3,2,1-ij]quinolin-1-yl)-4-(1H-indol-3-yl)pyrrolidine-2,5-dione (compound A (trans racemate))

A solution of the crystals of compound B (80.0 g) obtained in Example 4, dissolved in THF (1440 mL) was degassed, and 5% palladium on carbon (Pd—C, 50% wet product, 8.0 g (in terms of dry content)) and a 1 M solution of potassium tert-butoxide in THF (205 mL) were added. The atmosphere in the system was replaced with nitrogen gas to remove oxygen, and then, hydrogen gas was injected. The procedure of replacing the system with nitrogen gas and injecting hydrogen gas was repeated three times. Then, the hydrogen pressure was adjusted to approximately 450 kPaG at which the reaction mixture was stirred at about 58° C. to about 65° C. for about 6 hours. After the completion of reaction, the reaction mixture was cooled to about 20° C. to about 30° C., and hydrogen in the system was removed and replaced with nitrogen gas. To the reaction mixture, 2 M hydrochloric acid (320 mL) was added. Then, the Pd catalyst was filtered off, and the residue containing compound A (trans racemate) was washed with THF (400 mL). The filtrate and the washes containing compound A (trans racemate) were combined. Isopropyl acetate (640 mL) and water (160 mL) were added, and the mixture was stirred at room temperature and then separated into aqueous and organic layers. The aqueous layer was removed, and the organic layer containing compound A (trans racemate) was obtained. To the organic layer containing compound A (trans racemate), 10% saline (400 mL) was added, and the resulting mixture was stirred at room temperature and then separated into aqueous and organic layers. The aqueous layer was removed. The obtained organic layer containing compound A (trans racemate) was concentrated to about 400 mL or less under a reduced pressure at an internal temperature of about 40° C. or lower, and isopropyl acetate (1360 mL) was added. The resulting solution containing compound A (trans racemate) was further concentrated to 1200 mL under a reduced pressure at an internal temperature of about 40° C. or lower, and isopropyl acetate (1200 mL) was added. The resulting solution was concentrated again to 1200 mL under a reduced pressure at an internal temperature of about 40° C. or lower. Then, heptane (2000 mL) was added dropwise at an internal temperature of about 15° C. to about 30° C. over about 30 minutes or longer. The mixture was stirred at the same temperature as above for about 2 hours or longer. The deposited crystals of compound A (trans racemate) were collected by filtration and washed with heptane (400 mL). The obtained crystals compound A (trans racemate) were dried in vacuum at about 50° C. for about 12 hours or longer (85.3 g, yield: 92.8%).

Example 6

Comparative Example

Compound B was produced in the same way as in Steps 1 and 2 of Example 3 except that t-BuOK was added dropwise to a solution of the compounds C and D of Example 3. Furthermore, (3R,4R)-compound A was produced in the same way as in Step 3 through Step 5 of Example 3. The purity of compound B obtained from Example 3 and the Comparative Example and the impurity level are shown in Table 1. The purity of (3R,4R)-compound A obtained from Example 3 and the Comparative Example and the impurity level are shown in Table 2.

TABLE 1

Purity of compound B and content of impurities

| | Measurement by Example 7 | | Measurement by Example 8 Assay of Impurity 2 (wt %) |
|---|---|---|---|
| | HPLC Peak Area (%) of compound B | HPLC Peak Area (%) of Impurity 1 | |
| Comparative Example | 90.4 | 7.8 | 10.7 |
| Example 3 | 95.0 | 0.1 | 5.3 |
| Example 4* | 97.5 | 0.2 | 3.3 |

Impurity 1 = 5,6-dihydro-4H-pyrrolo[3,2,1-ij]quinolin-1-yl-oxoacetamide
Impurity 2 = oligomeric by-products
*= unpurified crystals

TABLE 2

Purity of (3R,4R)-compound A and content of impurities

| | Measurement by Example 7 | | Measurement by Example 8 Assay of Impurity 2 (wt %) |
|---|---|---|---|
| | HPLC Peak Area (%) of (3R,4R)-compound A | HPLC Peak Area (%) of Impurity 1 | |
| Comparative Example | 99.9 | <0.1 | 1.0 |
| Example 3 | 99.9 | <0.1 | 0.2 |

Impurity 1 = 5,6-dihydro-4H-pyrrolo[3,2,1-ij]quinolin-1-yl-oxoacetamide
Impurity 2 = oligomeric by-products Example 7

Measurement Conditions of Liquid Chromatography (Purity Measurement Conditions)

Detection: UV 270 nm,
Column: Symmetry C18 (4.6×250 mm, 5 pin, Waters Corp.),
Column temperature: 25° C.,
Flow rate: 1.0 mL/min,
Elution solvents: (A) water (containing 0.05% trifluoroacetic acid) and (B) acetonitrile (containing 0.05% trifluoroacetic acid),
Gradient conditions:
  Time: start of measurement→after 20 minutes into measurement, B/(A+B): 45%→80%,
  Time: 20 min→25 min, B/(A+B): 80%→95%,
  Time: 25 min→30 min, B/(A+B): 95%,
  Time: 30 min→30.01 min, B/(A+B): 95%→45%.
The impurity at retention time 0.5 minutes was identified as 5,6-dihydro-4H-pyrrolo[3,2,1-ij]quinolin-1-yl-oxoacetamide (impurity 1).

Example 8

Measurement Conditions of Liquid Chromatography (Purity Measurement Conditions)

Column: TSKgel G25000PWXL (7.8×300 mm, 7 μm, TOSOH CORP.),
Detection: UV 210 nm,
Column temperature: 40° C.,
Flow rate: 0.5 mL/min,
Elution solvent: acetonitrile/water (1/1, v/v)
The impurity having a broad peak at retention times of 9 to 22 minutes was identified as oligomeric by-products (impurity 2).

The invention claimed is:
1. A method for preparing a highly pure pyrroloquinolinyl-pyrrole-2,5-dione having a purity of at least 90%, or a pharmaceutically acceptable salt or diastereomer thereof, comprising:
  (a) dissolving a methyl pyrroloquinolinyl-oxoacetate and an acetamide in an organic solvent to form a solution;
  (b) adding the solution in (a) to a base; and
  (c) reacting the methyl pyrroloquinolinyl-oxoacetate and the acetamide,
wherein the highly pure pyrroloquinolinyl-pyrrole-2,5-dione, or a pharmaceutically acceptable salt or diastereomer thereof is prepared.
2. The method of claim 1, wherein the organic solvent is an ether, a hydrocarbon, or an amide.

3. The method of claim 1, wherein the organic solvent is an ether.

4. The method of claim 1, wherein the organic solvent is dimethyl ether, diethyl ether, tetrahydrofuran, toluene, hexane, dimethylformamide, or dimethylacetamide.

5. The method of claim 1, wherein the organic solvent is tetrahydrofuran.

6. The method of claim 1, wherein the base is an inorganic base or a metal base.

7. The method of claim 1, wherein the base is a metal hydroxide or a metal alkoxide.

8. The method of claim 1, wherein the base is an metal alkoxide.

9. The method of claim 1, wherein the base is sodium hydroxide, potassium hydroxide, potassium tert-butoxide, sodium tert-butoxide, lithium hexamethyldisilazide, sodium hexamethyldisilazide, or lithium diisopropylamide.

10. The method of claim 1, wherein the base is potassium tert-butoxide.

11. The method of claim 1, wherein the base is dissolved or suspended in an organic solvent.

12. The method of claim 11, wherein the organic solvent is an ether, a hydrocarbon, or an amide.

13. The method of claim 11, wherein the organic solvent is an ether.

14. The method of claim 11, wherein the organic solvent is tetrahydrofuran.

15. The method of claim 1, wherein the ratio between the amount of the acetamide and the amount of methyl pyrroloquinolinyl-oxoacetate is 0.5-2.0.

16. The method of claim 1, wherein the ratio between the amount of the base and the amount of methyl pyrroloquinolinyl-oxoacetate is 1.0-10.

17. The method of claim 1, wherein the temperature of the reaction in (c) is 10-65° C.

18. The method of claim 1, further comprising step (d): reducing the pyrroloquinolinyl-pyrrole-2,5-dione to a pyrroloquinolinyl-pyrrolidine-2,5-dione.

19. The method of claim 1, wherein the methyl pyrroloquinolinyl-oxoacetate is methyl 5,6-dihydro-4H-pyrrolo[3,2,1-ij]quinolin-1-yl-oxoacetate.

20. The method of claim 1, wherein the acetamide is indole-3-acetamide.

21. The method of claim 1, wherein the pyrroloquinolinyl-pyrrole-2,5-dione is 3-(5,6-dihydro-4H-pyrrolo[3,2,1-ij]quinolin-1-yl)-4-(1H-indol-3-yl)-1H-pyrrole-2,5-dione.

22. The method of claim 18, wherein the pyrroloquinolinyl-pyrrolidine-2,5-dione is 3-(5,6-dihydro-4H-pyrrolo[3,2,1-ij]quinolin-1-yl)-4-(1H-indol-3-yl)pyrrolidine-2,5-dione.

23. The method of claim 22, wherein the 3-(5,6-dihydro-4H-pyrrolo[3,2,1-ij]quinolin-1-yl)-4-(1H-indol-3-yl)pyrrolidine-2,5-dione is (3R,4R)-3-(5,6-dihydro-4H-pyrrolo[3,2,1-ij]quinolin-1-yl)-4-(1H-indol-3-yl)pyrrolidine-2,5-dione.

24. A method for preparing a highly pure pyrroloquinolinyl-pyrrolidine-2,5-dione having a purity of at least 90%, or a pharmaceutically acceptable salt or diastereomer thereof, comprising:
   (a) dissolving a methyl pyrroloquinolinyl-oxoacetate and an acetamide in an organic solvent to form a solution;
   (b) adding the solution in (a) to a base;
   (c) reacting the methyl pyrroloquinolinyl-oxoacetate and the acetamide to produce a pyrroloquinolinyl-pyrrole-2,5-dione; and
   (d) reducing the pyrroloquinolinyl-pyrrole-2,5-dione to a pyrroloquinolinyl-pyrrolidine-2,5-dione,
wherein the highly pure pyrroloquinolinyl-pyrrolidine-2,5-dione, or a pharmaceutically acceptable salt or diastereomer thereof is prepared.

* * * * *